Figure 1:
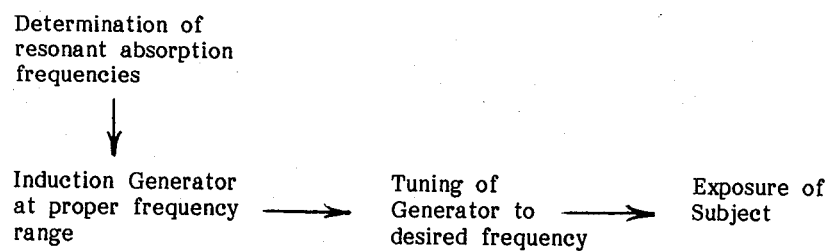

United States Patent [19]

Gordon

[11] Patent Number: 4,622,953
[45] Date of Patent: Nov. 18, 1986

[54] PROCESS FOR THE TREATMENT OF ATHEROSCLEROTIC LESIONS

[76] Inventor: Robert T. Gordon, 4936 W. Estes, Skokie, Ill. 60077

[21] Appl. No.: 781,782

[22] Filed: Sep. 30, 1985

Related U.S. Application Data

[60] Division of Ser. No. 681,697, Dec. 14, 1984, which is a continuation of Ser. No. 457,715, Jan. 13, 1983, abandoned, which is a continuation of Ser. No. 96,413, Nov. 21, 1979, abandoned.

[51] Int. Cl.$^4$ ............................................. A61N 1/42
[52] U.S. Cl. .................................... 128/1.3; 128/422; 604/20
[58] Field of Search ................ 128/1 R, 1.1, 1.3, 1.5, 128/422, 736, 804; 604/20, 21; 424/1.1, 9, 85, 147; 514/829, 889

[56] References Cited

U.S. PATENT DOCUMENTS

| | | | |
|---|---|---|---|
| 3,489,522 | 1/1970 | McConnell | 424/9 |
| 3,853,993 | 12/1974 | Gainer | 514/824 |
| 3,895,106 | 7/1975 | Morrison | 514/824 |
| 4,005,699 | 2/1977 | Bucalo | 128/1.3 |
| 4,027,021 | 5/1977 | Underwood | 514/889 |
| 4,359,453 | 11/1982 | Gordon | 128/1.1 |

Primary Examiner—William E. Kamm
Attorney, Agent, or Firm—Lalos, Keegan & Kaye

[57] ABSTRACT

A process for the treatment of atherosclerotic lesions by the application of external electromagnetic energy capable of achieving biophysical alterations in the intracellular structure of the lesions, including stimulation of intracellular production of interferon. The process accomplishes these biophysical alterations by tuning an external electromagnetic energy to the resonant energy absorption frequencies of the intracellular structure of the lesions and then exposing the subject to this tuned electromagnetic energy field. Alternatively, the field can be tuned to the frequency which has been calculated to be closest to the resonant frequency of the lesions and furtherest from the resonant frequency of the normal vascular cells. The process may be further enhanced by the intracellular absorption of selected materials designed to alter the magnetic susceptibility and therefore the resonant energy absorption frequency of the intracellular structure.

20 Claims, 2 Drawing Figures

PROCESS FOR THE TREATMENT OF ATHEROSCLEROTIC LESIONS

This is a division of co-pending application Ser. No. 681,697, filed Dec. 14, 1984 which is a continuation of Ser. No. 457,715 filed Jan. 13, 1983, now abandoned, which is a continuation of Ser. No. 096,413, filed Nov. 21, 1979, now abandoned.

This invention relates generally to a process for the treatment of cancer in living tissues and is an extension of the technology described in U.S. Pat. No. 4,106,488 issued Aug. 15, 1978; and U.S. Pat. No. 4,136,683 issued Jan. 30, 1979. More particularly, the present invention relates to method for achieving biophysical alterations in the intracellular structure of cells. These biophysical alterations include thermal changes, stimulation of the intracellular production of interferon, stimulation of the intracellular production of prostaglandins, and the treatment of cancer by intracellularly killing the cancer cells without injuring the normal cells.

BACKGROUND OF THE INVENTION

There are presently a number of methods and techniques for the treatment of cancer, among which may be included: radiation therapy, chemotherapy, immunotherapy, and surgery. The common characteristic for all of these techniques as well as any other presently known technique is that they are extracellular in scope; that is, the cancer cell is attacked and attempted to be killed through application of the killing force or medium outside of the cell; the only known exception being, U.S. Pat. No. 4,106,488, Cancer Treatment Method, Robert Thomas Gordon, issued Aug. 15, 1978, of which this invention is an extension of the technology therein described.

The extracellular approach is found to be less effective because of the difficulties of penetrating the outer membrane of the cancer cell that is composed of two protein layers with a lipid layer in between. Of even greater significance is that in order to overcome the protection afforded the cell by the cell membrane in any extracellular techniques, the attack on the cancer cells must be of such intensity that considerable damage is caused to the normal cells resulting in severe side effects upon the subject. These side effects have been found to limit considerably the effectiveness and usefulness of these extracellular treatments.

A safe and effective cancer treatment has been the goal of investigators for a substantial period of time. Such a technique to be successful in the destruction of the cancer cells must be selective in effect upon the cancer cells and produce no irreversible damage to the normal cells. In sum, cancer treatment must selectively differentiate cancer cells from normal cells and must selectively weaken or kill the cancer cells without affecting the normal cells.

It has been known that there are certain physical differences that exist between cancer cells and normal cells. One primary physical difference that exists is the temperature differential characteristics between the cancer cells and the normal cells. Cancer cells, because of their higher rates of metabolism, have higher resting temperatures compared to normal cells. In the living cell, the normal temperature of the cancer cell is known to be 37.5° Centigrade, while that of the normal cell is 37° Centigrade. Another physical characteristic that differentiates the cancer cells from the normal cells is that cancer cells die at lower temperatures than do normal cells. The temperature at which a normal cell will be killed and thereby irreversibly will be unable to perform normal cell functions is a temperature of 46.5° Centigrade, on the average. The cancer cell, in contrast, will be killed at the lower temperature of 45.5° Centigrade. The temperature elevation increment necessary to cause death in the cancer cell is determined to be at least approximately 8.0° Centigrade, while the normal cell can withstand a temperature increase of at least 9.5° Centigrade.

It is known, therefore, that with a given precisely controlled increment of heat, the cancer cells can be selectively destroyed without injury to the normal cells. On the basis of this known differential in temperature characteristics, a number of extracellular attempts have been made to treat cancer by heating the cancer cells in the body. This concept of treatment is referred to as hyperthermia. To achieve these higher temperatures in the cancer cells, researchers have attempted a number of methods including inducing high fevers, utilizing hot baths, diathermy, applying hot wax, and even the implantation of various heating devices in the area of the cancer.

Presently, none of the various known approaches to treat cancer have been truly effective and all have the common characteristic of approaching the problem by treating the cancer cell extracellularly; the only known exception being, U.S. Pat. No. 4,106,488, Cancer Treatment Method, Dr. Robert Thomas Gordon, issued Aug. 15, 1978. The outer membrane of the cancer cell being composed of lipids and proteins, is a poor thermal conductor, thus making it difficult for the application of heat by external means to penetrate into the interior of the cell where the intracellular temperature must be raised to effect the death of the cell. If, through the extracellular approaches of the prior hyperthermia techniques, the temperatures were raised sufficiently to effect an adequate intracellular temperature to kill the cancer cells, many of the normal cells adjacent the application of heat would be destroyed as well.

It has been known that the nuclei of cancer cells and the nuclei of normal cells possess some differences. The alterations which occur in a cell to produce malignancy either take place in, or are transmitted to, the nucleus. This is evident by the fact that the cells produced by tumor cell multiplication possess the same characteristics as the original tumor cell.

A large amount of work has been done "in vitro" concerning the magnetic resonant frequencies of cancer tissues as compared to those of normal tissues. Differences have been attributed to differences in the amount of water present in the cancer cells and the way in which the water molecules are ordered. A key to this process lies in the nuclear differences, including energy changes characteristic of structural and conformational changes in the deoxyribonucleic acid and the histones of the nucleus, including their relationship, resulting in differential resonant frequencies for the cancer cells from the normal cells.

A further key to this process is the additional changes in intracellular biophysical characteristics which occur in this process. Included in these changes is the intracellular production of interferon and/or prostaglandins. The production of interferon in the past has been shown to be triggered by foreign agents or materials which alter the internal biophysical characteristics of the cell by increases in the intracellular temperature or energy levels.

Due to the unstable characteristics of interferon and prostaglandins, even if interferon and prostaglandins were to be synthesized and subsequently injected intravascularly into a subject, the effectiveness of the synthesized interferon and/or prostaglandins would be limited due to the loss of time between injection into the subject and the time when the synthesized interferon and/or prostaglandins would reach the cellular level where their effectiveness is required. Interferon and prostaglandins are most effective when their production is stimulated intracellularly so that their peak effectiveness and potential are utilized, where required, intracellularly.

OBJECT OF THE INVENTION

It is therefore the purpose and principal object of the present invention to selectively destroy cancer cells by achieving biophysical alterations in the intracellular structure of the cancer cells while producing no significant effects upon the normal cells. The biophysical alterations include thermal changes, the stimulation of the intracellular production of interferon and/or the stimulation of the intracellular production of prostaglandins. In addition, the present invention provides a technology for the detection of cancer cells wherever they exist in the body.

SUMMARY OF THE INVENTION

A treatment of cancer by the application of external electromagnetic energy capable of achieving biophysical alterations in the intracellular structure of cancer cells in living tissue. These biophysical alterations include thermal changes, the stimulation of intracellular production of interferon and the stimulation of intracellular production of prostaglandins. The process comprises accomplishing these biophysical alterations by tuning the external electromagnetic energy to the resonant energy absorption frequencies of the intracellular structure of the selected cells. Alternatively, the field can be tuned to the frequency which has been calculated to be closest to the resonant frequency of the cancer cells and furtherest from the resonant frequency of the normal cells. The process may be further enhanced by the intracellular absorption of selected materials designed to alter the magnetic susceptibility and therefore the resonant energy absorption frequency of the intracellular structure. The biophysical differences between diseased cells and normal cells make possible the selective absorption of materials thereby enhancing the differences in magnetic susceptibilities between diseased cells and normal cells resulting in an increased capability of selective energy absorption by diseased cells. This technology has diagnostic applications in the detection of cancer cells in combination with the use of differential resonant frequencies, magnetic resonance and electron spin resonance techniques. The process will have application in the treatment of a wide range of diseases at the cellular level, particularly, in the field of cancer where this mode of affecting the thermal characteristics and of stimulating the intracellular production of interferon and/or prostaglandins in the diseased cells will be effective in the selective destruction of cancer cells without injuring the normal cells and tissue.

Another object of the present invention is to determine and treat atherosclerotic lesions without affecting the normal vessel wall.

THE DRAWINGS

FIG. 1 is a flow chart illustrating one method of treating atherosclerotic lesions at their resonant frequencies according to the present invention.

Figure 2:
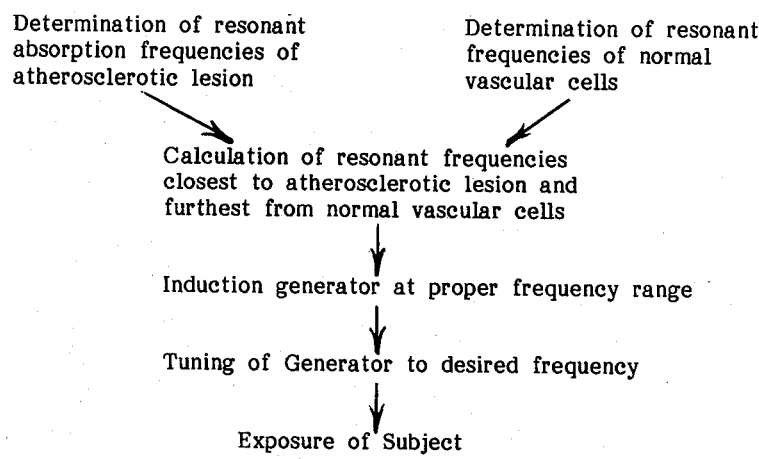

FIG. 2 is a flow chart illustrating a second method of treating atherosclerotic lesions at their optimal resonance frequencies in relation to the normal resonance frequencies for vascular cells. As described in detail later, this process can be enhanced by the use of intracellular particles to enhance the difference in resonance frequencies between atherosclerotic lesions and normal vascular cells. These particles can be located in the atherosclerotic lesions, in the normal vascular cells, or both.

DESCRIPTION OF THE INVENTION

The present invention achieves a precise increment of heat rise within the cancer cell and within the cytoplasm. The thermal barrier that characteristically exists as the outer membrane or cell wall of the cell is now utilized as a means of retaining the heat produced within the cell, rather than, as in the past, preventing any heat build-up within the cell. On the basis of the cell resting temperatures and the temperature necessary to produce cell death, the increment that the cell temperature must be raised to cause the cell death is critical. For the normal cell, the temperature rise is 9.5° Centigrade, while in the cancer cell the temperature rise is approximately 8.0° Centigrade. Thus, any temperature rise in the cancer cell or in the normal cell that is at least 8.0° Centigrade and not more than 9.5° Centigrade above the normal cell temperature results in the selective destruction of the cancer cell without any harmful effects to the normal cell.

In accordance with the present invention, there are found to be a number of approaches that can successfully achieve the end result of an intracellular heat rise and an intracellular destruction of the cancer cell.

In its simplest and broadest aspect, the invention contemplates the use of the differential resonant frequencies of cancer cells and normal cells to allow significant energy absorption into the cancer cells at their specific resonant frequency while allowing very little energy absorption into the normal cells. The nuclei of the cancer cells (the DNA, histones, etc.) besides often being different in content, usually differ in conformation and binding from the nuclei of normal cells (the DNA, histones, etc.). These differences contribute to the variance in the resonant frequencies between the structures in cancer cells and in normal cells. This difference between the cancer cells and the normal cells being nuclear in origin, is transmitted to the daughter cancer cells formed by cell division and explains the daughter cells' propensity towards malignancy.

A tuning fork will resonate, absorbing energy, from sound produced by another tuning fork of the same pitch (frequency) twenty or thirty feet away. If a variety of structures were placed within the effective range of a high frequency electromagnetic field, those structures having the same resonant frequency as the electromagnetic field will absorb energy from the field. Therefore, by placing the subject within the effective range of the high frequency electromagnetic field and by tuning the frequency of this field to the specific resonant frequency of the cancer cells, the cancer cells will then absorb energy from this electromagnetic field resulting in the raising of their intracullular temperature and the affecting of their biophysical properties so as to selectively destroy the cancer cells without affecting the normal cells.

Computerized axial tomography techniques are combined with an electromagnetic field generator and detection receiver sensing techniques to obtain three-dimensional data on specific point resonant energy absorption at a range of frequencies. The resonant frequency of the cancer cells being different from that of the normal cells will serve to identify the location of the cancer cells.

One possible configuration would embody the subject being placed within a large helical coil and the entire coil energized by a high frequency generator so that the entire subject would be within the effective range of this electromagnetic field. The frequency of this electromagnetic field would be selected as the one closest to the resonant frequency of the cancer cells and furthest from that of the normal cells. The cancer cells will absorb energy at their resonant frequency and will be destroyed intracellularly while the normal cells are unharmed.

This destruction of the cancer cells can be monitored by repeating the first part after completion of the second in order to monitor the destruction of the cancer cells. This destruction can be monitored by observing the absence of cells which absorb energy at the cancer cells resonant frequency.

This technology has application in the treatment of Atherosclerosis. Research work by the inventor and studies in the literature suggest that the development of atherosclerotic lesions is in many ways similar to tumor formation with the multiplication of a single cell line and the proliferation of smooth muscle cells (the monoclonal theory). These proliferating smooth muscle cells along with the deposition of cholesterol allow the components of the atherosclerotic plaque to have resonant frequencies different from those of the normal intimal wall. The magnetic resonant frequencies of lipids in bilayers and membranes as well as of phospholipids in relation to membrane permeability (which of course is very important to this discussion of atherosclerosis), have been studied. Membrane perturbations by physical agents can actually be followed using electron spin probe analysis. Using selective irradiation of the specimen in switched magnetic field gradients, blood flow in a vessel can be measured due to the different spin characteristics of the new polarized blood entering a specific region of the vessel. Studies by the inventor along with others found in the literature, illustrate the changes in the newly formed atherosclerotic plaques.

Therefore by peforming a three-dimensional scan utilizing magnetic resonant sensing techniques, the areas of atherosclerotic lesions may be identified. Subsequently by subjecting the subject to the frequency closest to the resonant frequency of the atherosclerotic lesions, the lesions may be destroyed due to the absorption of energy, without affecting the normal vessel wall whose cells respond to a different set of frequencies.

The uptake of particles by tumors and atherosclerotic plaques in certain stages of their formation has been demonstrated. Magnetic resonant sensing techniques may be utilized to characterize the magnetic parameters of the structures. Electron spin probe analysis has been used to detect membrane perturbation by physical agents. By allowing the tumor or atherosclerotic plaque to take up the particles, be they ferromagnetic, paramagnetic, or diamagnetic, the process of determining the resonant frequencies of the cancer cells or the atherosclerotic lesions and of energy absorption at the desired resonant frequency, may be enhanced.

The production of interferon is triggered by a foreign substance which the cell senses. A magnetically excitable particle which is absorbed intracellularly by the tumor cell and then magnetically excited, results in energy absorption, temperature rise, and some mechanical vibration, which acts to trigger and to stimulate interferon production as well as prostaglandins production in the cell and other intracellular immunological responses. These responses aid in the processes' ability to destroy the cancer cells. The intracellular absorption of resonant energy, alone, will excite and alter the intracellular biophysical characteristics and will stimulate the intracellular production of interferon and/or prostaglandins.

The intracellular absorption of agents other than magnetically excitable particles; i.e. various sugars, agents affecting cyclic-AMP, a material or materials capable of generating heat intracellularly by chemical reaction and/or the application of an increased oxygen supply to the cells resulting in an increased rate of chemical reaction and increased intracellular metabolism can also be utilized to alter the magnetic susceptibility of the cell and to help the absorption of energy at the cancer cell's resonant frequency. The intracellular production of interferon, prostaglandins, and other immunological agents, is also stimulated. The intracellular absorptions enhance the difference in the resonant frequencies between the cancer cells and the normal cells as well as to affect the magnetic susceptibility of the cell thereby enhancing the processes in this invention to selectively destroy cancer cells.

The cancer cells and the normal cells metabolic rate and activity are affected differently by agents such as sugars, prostaglandins, interferon, and agents affecting cyclic-AMP as well as by the intracellular resonant energy changes, themselves. This differential response of the cancer cells and normal cells metabolic activity allows for a variation with time in the respective resonant frequencies of the cancer cells and the normal cells. These differences can be utilized in choosing the specific time when the resonant frequencies of the cancer cells and the normal cells differ the most so as to enhance the process of detecting cancer cells and the process of selectively killing the cancer cells without injuring the normal cells and tissues.

EXAMPLE I

Determination of resonant energy absorption frequency for materials or tissues is obtained by using a high frequency signal generator with the capability of sweeping the frequency range to be scanned which is connected to an antenna. A receiving coil connected to a power meter (so as to measure the power received) is placed a short distance away. The material or tissues (whose resonant absorption frequency is to be determined) is placed in the space between the transmitting antenna and the receiving coil. Appropriate shielding is placed laterally around the specimen being tested in such a manner that any RF energy being transmitted from the antenna to the receiving coil must pass through the specimen. As the frequency range of the signal generator is scanned and the power received by the coil is measured, the resonant absorption frequency for the specimen being tested will be indicated by a significant drop in the power received by the receiving coil (since at this resonant frquency, the specimen will be absorbing some of the power).

This method will be applicable to determining different resonant absorption frequencies for cancer cells and for normal cells and for the various additive materials. The method will also be useful in measuring the alteration of the resonant absorption frequency by the intracellular absorption of various materials and by changes in the intracellular metabolic rate.

EXAMPLE II

As a specific example of the simplest form of the present invention, prior to treateament, tumor tissue biopsies are taken and examined under light microscopy to confirm tumor cell identification. 2 cc. of an aqueous colloidal solution of FeOOH and dextran is injected intravenously into the subject. This solution when injected intravenously is capable of being intracellularly absorbed and thus greatly increases the magnetic susceptibility of the intracellular structure of the cell. Moreover, after this solution is intracellularly absorbed, it is capable of being metabolized by the cell thus producing a variable magnetic susceptibility with reference to time. Biopsies taken several hours after the intravenous injection of the solution and examined under electron microscopy, confirm the intracellular absorption of this solution, particularly by the cancer cells. Biopsies of cancer tissue and normal tissue taken at 1 hour, 2 hours, 4 hours, 12 hours, 24 hours, and 48 hours after the intravenous injection of this solution are immediately frozen and subsequently taken for measurements of magnetic susceptibility in a Vibrating Sample Magnetometer, Princeton Applied Research Model No. 159. Using this data, it is possible to plot the rise in magnetic susceptibility due to the intracellular absorption of the solution in the cancer cells and to compare it to the magnetic susceptibility changes in the normal cells. This gives data on the increase in magnetic susceptibility not only due to the intracellular absorption of the solution, but also with reference to the metabolism in the time period. Using frozen samples from a time period which indicates high relative magnetic susceptibility of cancer cells to normal cells, and using the method described in Example I earlier, for determining the optimal resonant absorption frequency, it was determined that a high frequency electromagnetic field of 450 kilohertz applied approximately 4 hours after the intravenous injection of this solution, would provide optimal resonant energy absorption and resultant biophysical alterations by the cancer cells. Approximately 48 hours after this procedure was followed, biopsies were taken and examined under light microscopy and electron microscopy which confirmed the effectiveness of this procedure in destroying cancer cells without injurying surrounding normal cells and normal tissue.

EXAMPLE III

Basically this invention relates to achieving biophysical alterations in the intracellular structure of living cells, particularly cancer cells, by raising the energy level inside the cells, intracellularly. The application of energy derived from chemical reaction can be utilized for this purpose, for example; ferric oxyhydroxide particles of 0.7 micron size are colloidally suspended in a 5% dextrose aqueous solution in an amount of approximately 50 mg. of the particles per cc. Dosages in the amount of 30 mg. per kg. of body weight of the subject are intravenously injected. Techniques described in U.S. Pat. No. 4,106,488 may be employed to more selectively direct the particles to the cancer cells. Approximately 4 hours after injection, particles will have been intracellularly absorbed by the cancer cells. Subject is then placed in a hyperbaric oxygen chamber and subjected to an approximate 50% oxygen concentration at a pressure of 3 atmospheres for a period of approximately 3 hours. Normal hyperbaric chamber safety procedures in achieving compression and decompression would be followed.

The hyperbaric oxygen chamber procedure would serve to raise the oxygen level of the subject's blood which, in turn, would raise the rate of intracellular absorption of oxygen. The increased rate of intracellular oxygen absorption, especially by the cancer cells, coupled with the already intracellularly absorbed ferric oxyhydroxide, results in an increased rate of oxidation and metabolism of the ferric oxyhydroxide and therefore in a significant rise in intracellular energy. This significant rise in intracellular energy further results in intracellular thermal changes, stimulates the intracellular production of interferon and/or stimulates the intracellular production of prostaglandins, resulting in a destruction of cancer cells wherever they exist in the subject.

EXAMPLE IV

The subject is placed on a table with the electromagnetic energy transmitter on one side and the detection receiver on the opposite side. The transmitter and the receiver are on a movable axis which can rotate 360° and move laterally the length of the subject. The frequency is varied from 1 Kilohertz to 50 Megahertz at each point on the 360° circle. The input from the detection receiver is fed into a computer which composes a three-dimensional picture of the resonant frequencies of all points in the subject. The distribution of cancer cells is noted as is their resonant frequency.

The subject is then placed in a large coil approximately 3 feet–6 feet in diameter. The coil is energized at the frequency determined by the computer. The subject is then treated for an increment of time determined from computer data. This increment of time could range from 2 minutes–30 minutes. Approximately 48 hours later, the subject is placed back on the original table and the procedure of detection repeated. Should any cancer cells with their specific resonant frequency be detected, then the subject is treated again, etc.

There are many variations of the invention as described and this invention should be limited solely by the scope of the following claims.

I claim:

1. A process for the treatment of atherosclerotic lesions comprising the steps of:
   determining the resonant absorption frequencies of said lesions,
   generating an electromagnetic field,
   tuning said electromagnetic field to said absorption frequencies of said lesions,
   exposing the subject to said tuned field to achieve biophysical alteration in said lesions' intracellular structures, and
   said biophysical alteration including the stimulation of intracellular production of interferon.

2. The process according to claim 1 further comprising the step of:
   intravenously injecting into the tissue of the subject metabolic and activity varying substances to alter the biophysical characteristics of the intracellular structure of said lesions.

3. The process according to claim 1 further comprising the step of:
introducing into the subject intracellular chemically generated energy substances to stimulate the intracellular production of interferon.

4. The process according to claim 1 further comprising the step of:
identifying the areas of atherosclerotic lesions in other areas of the subject by using said resonant absorption frequencies.

5. A process for the treatment of atherosclerotic lesions comprising the steps of:
determining the resonant absorption frequencies of said lesions,
determining the resonant absorption frequencies of the normal vascular cells of said subject,
calculating the frequency closest to said resonant frequency of said lesions and furtherest from said resonant frequency of said normal vascular cells,
generating an electromagnetic field,
tuning said electromagnetic field to said calculated frequency,
exposing the subject to said tuned field to achieve biophysical alteration in said lesions' intracellular structures, and
said biophysical alteration including the stimulation of intracellular production of interferon.

6. The process according to claim 5 further comprising the step of:
intravenously injecting into the subject metabolic and activity varying substances to alter the biophysical characteristics of the intracellular structure of the normal vascular cell.

7. The process according to claim 5 further comprising the step of:
intravenously injecting into the tissue of the subject metabolic and activity varying substances to alter the biophysical characteristics of the intracellular structure of said lesions.

8. The process according to claim 5 further comprising the step of:
introducing into the subject intracellular chemically generated energy substances to stimulate the intracellular production of interferon.

9. The process according to claim 5 further comprising the step of:
identifying the areas of atherosclerotic lesions in other areas of the subject by using said resonant absorption frequencies.

10. A process for the treatment of atherosclerotic lesions comprising the steps of:
determining the resonant absorption frequencies of the lesions,
generating an electromagnetic field,
tuning said electromagnetic field to said absorption frequencies of said lesions, and
exposing the subject to said tuned field to achieve biophysical alteration in said lesions' intracellular structures, including the intracellular heat rise of said lesions.

11. A process for the treatment of atherosclerotic lesions comprising the steps of:
determining the resonant absorption frequencies of the lesions,
generating an electromagnetic field external of the subject,
tuning said electromagnetic field to said absorption frequencies of said lesions, and
exposing the subject to said tuned field to achieve biophysical alteration in said lesions' intracellular structures, including the stimulation of intracellular production of interferon.

12. A process for the treatment of atherosclerotic lesions comprising the steps of:
determining the resonant absorption frequencies of the lesions,
generating an electromagnetic field,
tuning said electromagnetic field to said absorption frequencies of said lesions,
exposing the subject to said tuned field to achieve biophysical alteration in said lesions' intracellular structures, and
intravenously injecting into said tissue metabolic and activity varying substances to alter the biophysical characteristics of the intracellular structure of said lesions, including the magnetic susceptibility of said intracellular structure and therefore the resonant absorption frequency.

13. A process for the treatment of atherosclerotic lesions comprising the steps of:
determining the resonant absorption frequencies of the lesions,
determining the resonant absorption frequencies of the normal vacular cells of said subject,
calculating the frequency closest to said resonant frequency of said lesions and furtherest from said resonant frequency of said normal vascular cells,
generating an electromagnetic field,
tuning said electromagnetic field to said calculated frequency, and
exposing the subject to said tuned field to achieve biophysical alteration in said lesions' intracellular structures, including the intracellular heat rise of said lesions.

14. A process for the treatment of atherosclerotic lesions comprising the steps of:
determining the resonant absorption frequencies of the lesions,
determining the resonant absorption frequencies of the normal vascular cells of the subject,
calculating the frequency closest to said resonant frequency of said lesions and furtherest from said resonant frequency of said normal vascular cells,
generating an electromagnetic field external of said subject,
tuning said electromagnetic field to said calculated frequency, and
exposing the subject to said tuned field to achieve biophysical alteration in said lesions' intracellular structures, including the stimulation of intracellular production of interferon.

15. A process for the treatment of atherosclerotic lesions comprising the steps of:
determining the resonant absorption frequencies of the lesions,
intravenously injecting into the subject metabolic and activity varying substances to alter the biophysical characteristics of the intracellular structure of the normal vascular cells,
said biophysical characteristics including the magnetic susceptibility of said intracellular structure and therefore the resonant energy absorption frequency, determining the resonant absorption frequencies of the normal vascular cells of said subject, calculating the frequency closest to said resonant frequency of said lesions and furtherest from said resonant frequency of said normal vascular cells, generating an electromagnetic field, tuning said electromagnetic field to said calculated frequency, and exposing the subject to said tuned field to achieve biophysical alteration in said lesions' intracellular structures, including the stimulation of intracellular production of interferon.

16. A process for the treatment of atherosclerotic lesions comprising the steps of:

intravenously injecting into the tissue of the subject metabolic and activity varying substances to alter the biophysical characteristics of the intracellular structure of the lesions, including the magnetic susceptibility of said intracellular structure and therefore the resonant absorption frequency, determining the resonant absorption frequencies of said lesions, determining the resonant absorption frequencies of the normal vascular cells of said subject, calculating the frequency closest to said resonant frequency of said lesions and furtherest from said resonant frequency of said normal vascular cells, generating an electromagnetic field, tuning said electromagnetic field to said calculated frequency, and exposing the subject to said tuned field to achieve biophysical alteration in said lesions' intracellular structures, including the stimulation of intracellular production of interferon.

17. A process for the treatment of atherosclerotic lesions comprising the steps of:

determining the resonant absorption frequencies of the lesions, injecting into the subject particles capable of being absorbed intracellularly to enhance the determination of the resonant absorption frequencies, determining the resonant absorption frequencies of the normal vascular cells of the subject, calculating the frequency closest to said resonant frequency of said lesions and furtherest from said resonant frequency of said normal vascular cells, generating an electromagnetic field, tuning said electromagnetic field to said calculated frequency, and exposing the subject to said tuned field to achieve biophysical alteration in said lesions' intracellular structures, including the stimulation of intracellular production of interferon.

18. A process for the treatment of atherosclerotic lesions comprising the steps of:

injecting into the subject particles capable of being absorbed intracellularly to enchance the determination of the resonant absorption frequencies of the lesions, determining the resonant absorption frequencies of said lesions, generating an electromagnetic field, tuning said electromagnetic field to said absorption frequencies of said lesions, and exposing the subject to said tuned field to achieve biophysical alteration in said lesions' intracellular structures, including the stimulation of intracellular production of interferon.

19. A process for the treatment of atherosclerotic lesions comprising the steps of:

determining a resonant absorption frequency of the lesions, generating an electromagnetic field, tuning said electromagnetic field to said absorption frequency of said lesions, and exposing the subject to said tuned field to achieve biophysical alteration in said lesions' intracellular structures.

20. A process for the treatment of atherosclerotic lesions comprising the steps of:

determining a resonant absorption frequency of said lesions, placing the subject within the effective range of an electromagnetic field, and generating said electromagnetic field tuned to said resonant absorption frequency, and thereby exposing the subject to the field to achieve biophysical alteration in the intracellular structures of said lesions.

* * * * *